United States Patent [19]
DiFranco

[11] Patent Number: 5,007,827
[45] Date of Patent: Apr. 16, 1991

[54] ORTHODONTIC TWEEZERS

[76] Inventor: Paul A. DiFranco, 511 W. Talcott, Parkridge, Ill. 60068

[21] Appl. No.: 378,005

[22] Filed: Jul. 11, 1989

[51] Int. Cl.$^5$ .............................................. A61C 3/00
[52] U.S. Cl. .......................................... 433/4; 294/99.2
[58] Field of Search .......................... 433/3, 4; 294/99.2

[56] References Cited

U.S. PATENT DOCUMENTS

| | | |
|---|---|---|
| 90,319 | 5/1869 | Somers . |
| 482,232 | 9/1892 | Delaney .............................. 294/99.2 |
| 721,480 | 2/1903 | Van Schott ..................... 294/99.2 X |
| 1,701,995 | 2/1929 | Anderson ............................ 294/99.2 |
| 2,595,683 | 5/1952 | Lo Monte ................................. 81/43 |
| 2,634,728 | 4/1953 | Dale ..................................... 128/354 |
| 2,876,778 | 3/1959 | Kees, Jr. .............................. 128/346 |
| 3,291,476 | 12/1966 | Calkin .................................. 269/254 |
| 3,686,762 | 8/1972 | Sutter ..................................... 433/3 |
| 3,986,265 | 10/1976 | Cusato ..................................... 433/4 |
| 4,487,580 | 12/1984 | Ridgeway ............................... 433/3 |
| 4,666,199 | 5/1987 | Cheh ............................. 294/99.2 X |
| 4,717,190 | 1/1988 | Witherspoon ....................... 294/99.2 |

Primary Examiner—Robert P. Swiatek
Assistant Examiner—Nicholas D. Lucchesi
Attorney, Agent, or Firm—Robert E. Browne; Thomas C. McDonough

[57] ABSTRACT

A cross-over type tweezer is disclosed for use in orthodontic work and other areas where a small item must be held securely and precisely. The tweezer includes a gripping jaw with members formed transversely to the main axis of the tweezers to assist in holding small items such as orthodontic braces.

3 Claims, 1 Drawing Sheet

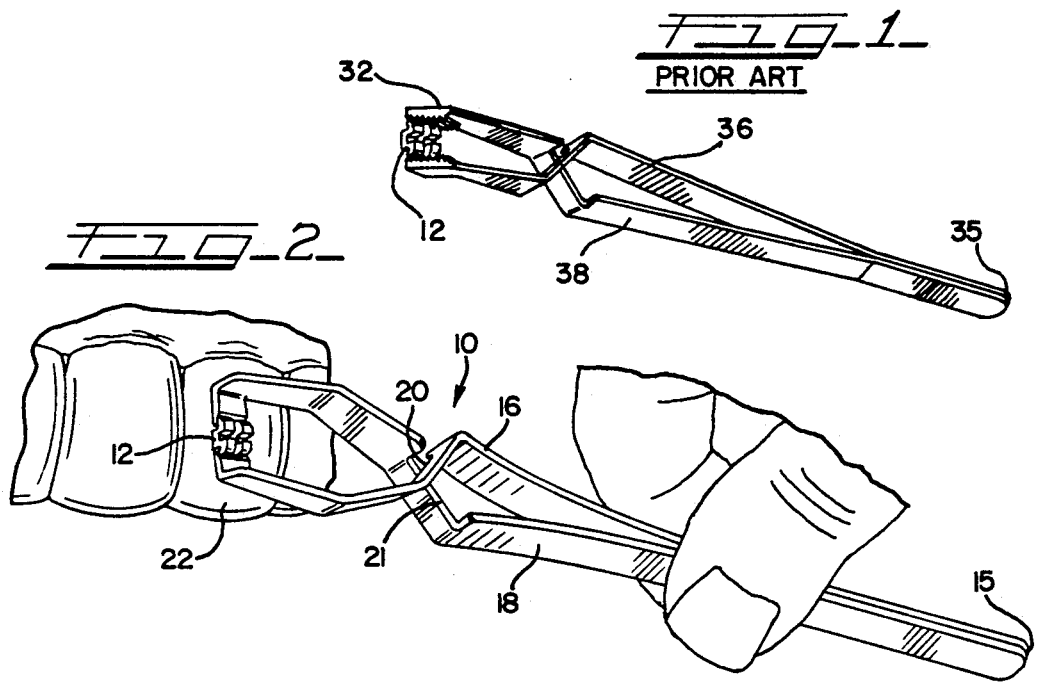
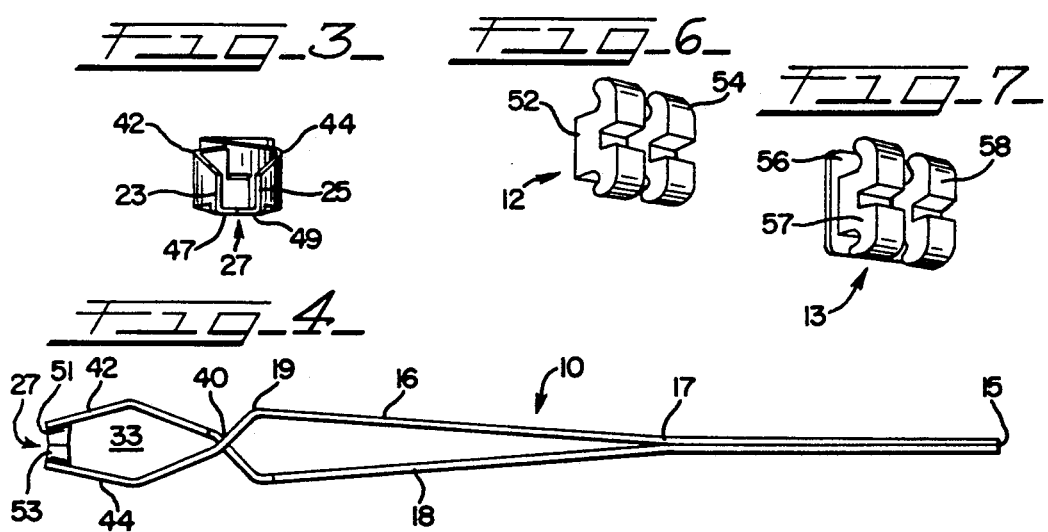
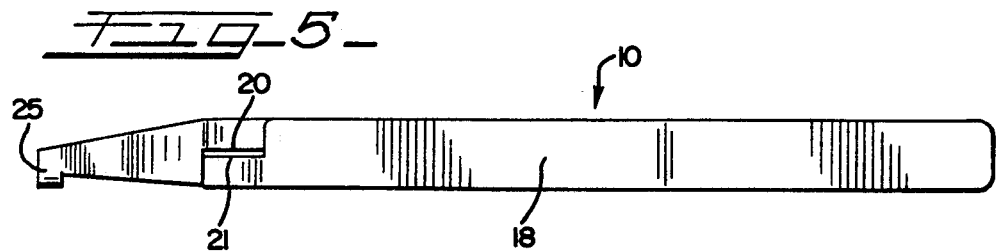

ORTHODONTIC TWEEZERS

BACKGROUND AND SUMMARY OF THE INVENTION

This invention relates to the design of tweezers, and more specifically to tweezers used for orthodontic work such as the placement of braces on teeth. Tweezers in accordance with the prior art are generally cumbersome and inadequate for use in such precise work, as the brace that must be attached to the patient's tooth is often quite small in comparison to the head or gripping area of the usual tweezers, and the brace must be held securely. In addition, tweezers in accordance with the prior art are not able to properly hold an orthodontic brace, as will be described below.

The tweezers in accordance with this invention generally comprise a cross-over type tweezers with gripper jaws at one end, with the gripper jaws formed to securely hold orthodontic braces parallel to the main axis of the tweezers. While the invention disclosed herein relates to tweezers designed specifically for use by an orthodontist in affixing braces to a patient's tooth, the tweezers could be used for other means.

Tweezers in accordance with the prior art generally are either of the crossover or pretensioned type, or the non-tensioned type. A non-tensioned tweezer has a gripping jaw which is not normally in the closed position, but rather must be closed by its user. The cross-over type, on the other hand, has a gripping jaw which is held in the closed position by tension formed into the tweezer's members by the shape of the tweezer. The user must apply pressure to the members to open the jaw, align the object upon which the tweezer is to be used with the gripping area, and then reduce the pressure on the members so that the object is held by the gripping area.

This cross-over type of tweezer is preferred over other designs for work requiring the object to be held securely and accurately, as the amount of force used to hold the object does not depend on the amount of pressure applied by the user, as it is in the previous design. This is especially crucial in the orthodontics field and in the placement of braces on the patient's teeth, because such braces are very small and must be held securely and located precisely. Orthodontic tweezers are used to hold the brace to the tooth until it can be secured thereto; thus it is essential that the orthodontist be able to maintain the brace securely in the gripping area of the tweezers. Therefore, the preferred embodiment of the tweezers in accordance with this invention use the cross-over design. However, this invention is not limited to such a tweezer, and could also embody a tweezer with arms that do not cross over one another.

There are two types of orthodontic braces relevant to this invention. The first is an anterior brace, designed for attachment to front teeth and comprising a center section, and wings at one end thereof. The opposite end of the center section is attached to the patient's tooth, and the slot receives and holds the wires that are used to connect the braces on adjacent teeth. The second type of brace is a posterior brace, designed for attachment to back teeth and comprising a center section, wings at one end thereof, and a base at the opposite end thereof. The base is slightly larger than the center section, and is concave to conform to the surface of the patient's tooth. A brace is glued to the patient's tooth, and it is crucial that this glue stays on the center section of an anterior brace, or the base of a posterior brace, and does not move up on to the wings. Glue under or on the wings prevents successful placement of the wires through the braces, and thus requires the removal of the brace.

However, current designs of cross-over type tweezers do not provide a gripping head that is adequate to securely hold an orthodontic brace and prevent glue from being accidentally placed on the wings. For example, U.S. Pat. No. 2,595,683, issued to Lo Monte, discloses a cross-over type tweezer using a means to adjust the tension between the arms. While this tweezer is useful for delicate work in picking up small objects, the head of the tweezer therein disclosed is not adequate for holding braces. Specifically, the long, narrow head of the Lo Monte tweezer, and tweezers similar to it, requires the orthodontist to hold the brace by the wings as he or she is attaching the brace to the tooth. Thus, there is nothing to prevent excess glue from contacting the wings. To overcome the flaws of earlier tweezer designs, the present invention contains a head with a gripping area that is transverse the axis of the tweezers and is formed to securely grip and hold a brace on the center section and behind the wings. Therefore, the center section or base may be glued to the tooth, and the gripping jaw of the tweezers actually blocks the flow of any excess glue from the tooth to the wings.

In addition, the wide and flat shape of the gripper jaws hold the brace more securely than do other designs of tweezers such as the Lo Monte tweezer described above, which generally have a gripping surface which is elongated along the same axis as the main body of the tweezers. These and further features of the preferred embodiment of this invention will be given in detail below.

BRIEF DESCRIPTION OF THE DRAWINGS

FIG. 1 is a perspective view of a tweezers in accordance with the prior art holding an anterior brace.

FIG. 2 is a view of the tweezers in accordance with this invention as it would be used by a orthodontist to hold an anterior brace to a patient's tooth.

FIG. 3 is an end view of the tweezers in accordance with this invention.

FIG. 4 is a top view of the tweezers in accordance with this invention.

FIG. 5 is an elevational view of the tweezers in accordance with this invention.

FIG. 6 is a perspective view of an anterior brace, as would be used by this invention.

FIG. 7 is a perspective view of a posterior brace, as would be used by this invention.

DETAILED DESCRIPTION OF THE DRAWINGS

As can be seen in FIG. 2, tweezer 10 is used by an orthodontist to hold brace element 12 to tooth 22 of the patient for securing the brace element thereto. The brace 12 shown in FIG. 2 is an anterior brace, which will be described in detail below. Tweezer 10 is comprised of two members 16 and 18, preferably made of a strong and durable material such as metal, although other materials could be used. Members 16 and 18 are formed in a shape as shown in FIGS. 2 and 4. They are joined at first end 15, and are securely connected to each other until first bend 17, where both members 16 and 18 are bent in opposite directions so that they move away from each other for a set distance. At second bend 19 members 16 and 18 cross over each other at crossover position 40 to form the gripping mechanism 33. The area between first bend 17 and second bend 19 is the area where the tweezers is held by the user.

At this cross-over position 40, member 16 has a bottom notch 20 formed therein while member 18 has a top notch 21 formed therein in a manner such that there is sufficient clearance for member 18 to cross over member 16 at the location of notches 20 and 21. This relationship between notches 20 and 21 can be seen most clearly in FIG. 5. It is to be understood, however, that the design of notches 20 and 21 is not crucial to the present invention, as other shapes and sizes of the notches could also be used.

Gripping mechanism 33 consists of the area between cross-over position 40 and the second end of the tweezer. Portion 42 of arm 18 and portion 44 of arm 16 are bent as shown in FIG. 4. The ends of portions 42 and 44 comprise the second end of the tweezer. As shown in FIGS. 3 and 4, the end of portion 42 is composed of first vertical member 23 and first horizontal member 47, which is integrally formed with and horizontal to vertical member 23. First horizontal member 47 is, therefore, transverse the longitudinal axis of the tweezers and faces inward. First horizontal member 47 has a flat top face 51.

The end of portion 44 is composed of second vertical member 25 and second horizontal member 49 which is integrally formed with and horizontal to second vertical member 25. Second horizontal member 49 is also formed transverse the longitudinal axis of the tweezers and facing inward towards first horizontal member 47. Second horizontal member 49 has a flat top face 53.

The first and second vertical members 23 and 25 and the first and second horizontal members 47 and 49 cooperate to form a U-shaped jaw 27. As can be seen most clearly in FIG. 5, first vertical member 23 (not shown) and second vertical member 25 extend below the plane of the gripping mechanism 33, so that jaw 27 is larger than the portion of the tweezer immediately next to it. Jaw 27 has a generally flat top face formed from the combination of the first and second flat top faces 51 and 53 of first and second horizontal members 23 and 25, respectively. Jaw 27 may be opened and closed, as described below.

The braces on which this invention is most advantageously used are shown in FIGS. 6 and 7. FIG. 6 shows an anterior brace, which contains a center section 52 and wings 54. FIG. 7 shows a posterior brace 13, which has a center section 57, wings 58, and a base 56. The shape of jaw 27 is critical to the invention, as it allows the dentist to securely hold an anterior brace 12 or posterior brace 13 behind the wings thereof. When used with an anterior brace, first horizontal member 47 and second horizontal member 49 of jaw 27 are placed against the sides of center section 52 and the jaw is closed. The brace 12 may then be placed against and bonded to the patient's tooth as shown in FIG. 2. The placement of jaw 27 between the tooth 22 and the wings 54 of the anterior brace or between the base 56 and wings 58 of a posterior brace prevents the bonding material from being accidentally moved from the center section to the wings by blocking any such flow of the bonding material. The presence of bonding material on the wings requires the removal of the brace and the placement of a new brace. The design of jaw 27 also allows the brace to be held securely for precise placement on the patient's tooth.

The shape of the tweezer, in conjunction with the material from which it is constructed, creates a tension in members 16 and 18 which forces the ends of portions 42 and 44 of gripping mechanism 33 to close upon one another. The user holds the tweezer between first bend 17 and second bend 19, and applies pressure thereto on each member in a direction inward towards the longitudinal axis. This pressure causes the jaw 27 to open to enable the user to engage a brace. As pressure on members 16 and 18 is lessened, jaw 27 is closed due to the above-mentioned tension present in the members. This enables the user to hold the brace within tweezer jaw 27 without continuing to apply pressure to members 16 and 18. However, it is to be understood that the crossover design of the tweezer as shown in FIGS. 2-5 is not crucial to the invention, and other shapes of the tweezer could also be used. For example, the tweezer in accordance with this invention could have two arms that do not cross over one another and thus require constant pressure to maintain the grip on the brace.

A tweezer 30 in accordance with the prior art is shown in FIG. 1. Prior art tweezer 30 is composed of two members 36 and 38 formed into the cross-over shape. A novel difference between prior art tweezer 30 and the present invention is in the shape of the gripping area or jaw, as described above. Prior art tweezer 30 has an elongated jaw 32 which is shaped to be most useful in picking up very small items. However, the design of jaw 32 is not conducive to securely and accurately holding an anterior or posterior brace in a steady and precise manner as shown in FIG. 2, and it is clearly inferior to the U-shaped jaw 27 of the present invention. Specifically, FIG. 1 shows a prior art tweezer 30 holding an anterior brace. This type of grip makes precise placement of the brace difficult, as it is difficult to have a secure grip on the brace. In addition, there is nothing preventing the glue from flowing from the tooth up to the wings.

It is to be understood that the above description is limited to a preferred embodiment of this invention, and should not be read to limit the invention in any manner. This invention should be read as limited by its claims only.

I claim:

1. In a tweezer comprising a pair of generally flat elongated members placed in an adjacent lengthwise relationship with one another, each member having a first end and a second end, the first ends of the members being fixably secured to one another, the first member and the second member crossing over one another between said first ends and said second ends, wherein the improvement comprises:

a first means for gripping integrally formed at the second end of the first member, the first means for gripping including a first vertical member having a first peripheral edge extending generally in the direction of the longitudinal axis of the tweezer and a first horizontal member extending inwardly from the first vertical member at said first peripheral edge;

and a second means for gripping being integrally formed at the second end of the second member, the second means for gripping including a second vertical member having a second peripheral edge extending generally in the direction of the longitudinal axis of the tweezer and a second horizontal member extending inwardly from the second vertical member at said second peripheral edge thereof, towards the first horizontal member, whereby the first and second means for gripping cooperate to form a U-shaped gripping jaw adapted to grip an orthodontic brace behind the wings of the brace for placement of the brace on a tooth.

2. A tweezer comprising:

a pair of generally flat elongated members placed in an adjacent relationship with one another, each member having a first and a second end, the first ends being fixably secured to one another, the second ends of the members being separated from one another, the first member crossing over said second member between said first ends and said second ends;

a first means for gripping integrally formed at the second end of the first member, the first means for gripping including a vertical member having a first peripheral edge extending generally in the direction of the longitudinal axis of the tweezer and a first horizontal member extending inwardly from the vertical member at said first peripheral edge thereof; and a second means for gripping being formed at the second end of the second member, the second means for gripping including a second vertical member having a second peripheral edge extending generally in the direction of the longitudinal axis of the tweezer and a second horizontal member extending inwardly at said second peripheral edge said thereof, and towards the first horizontal member, whereby the first and second means for gripping cooperate to form a U-shaped gripping jaw adapted to grip an orthodontic brace behind the wings of the brace for placement of the brace on a tooth.

3. A tweezer in accordance with claims 1 or 2 wherein the members are generally flat and vertically oriented when they are in the position relative to one another.

* * * * *